US006994845B2

(12) United States Patent
Mattai et al.

(10) Patent No.: US 6,994,845 B2
(45) Date of Patent: Feb. 7, 2006

(54) SOFT SOLID COMPOSITIONS WITH REDUCED SYNERESIS

(75) Inventors: Jairajh Mattai, Piscataway, NJ (US); Suman Chopra, Dayton, NJ (US); Lin Fei, Kendall Park, NJ (US); Eric Guenin, Pennington, NJ (US)

(73) Assignee: Colgate-Palmolive Company, New York, NY (US)

( * ) Notice: Subject to any disclaimer, the term of this patent is extended or adjusted under 35 U.S.C. 154(b) by 396 days.

(21) Appl. No.: 10/409,338

(22) Filed: Apr. 8, 2003

(65) Prior Publication Data

US 2004/0202629 A1    Oct. 14, 2004

(51) Int. Cl.
  A61K 7/32    (2006.01)
  A61K 7/34    (2006.01)
  A61K 7/36    (2006.01)
  A61K 7/38    (2006.01)
  A61K 7/00    (2006.01)

(52) U.S. Cl. .................. 424/65; 66/67; 66/68; 66/400; 66/401

(58) Field of Classification Search ............... 424/65, 424/66, 67, 68, 400, 401

See application file for complete search history.

(56) References Cited

U.S. PATENT DOCUMENTS

| 4,526,780 | A  | 7/1985  | Marschner et al. |
| 4,937,069 | A  | 6/1990  | Shin |
| 5,019,375 | A  | 5/1991  | Tanner et al. |
| 5,069,897 | A  | 12/1991 | Orr |
| 5,225,188 | A  | 7/1993  | Abrutyn et al. |
| 5,599,533 | A  | 2/1997  | Stepniewski et al. |
| 5,718,890 | A  | 2/1998  | Putnam et al. |
| 6,375,937 | B1 | 4/2002  | Chopra et al. |
| 2003/0022573 | A1 | 1/2003 | Cintio et al. |
| 2003/0022574 | A1 | 1/2003 | Pesce et al. |

FOREIGN PATENT DOCUMENTS

| EP |     0512 770 B1 | 10/1996 |
| EP |     0787 758 B1 | 8/1997  |
| WO | WO 92/19221     | 11/1992 |
| WO | WO 97/16161     | 5/1997  |
| WO | WO 97/16162     | 5/1997  |
| WO | WO 97/44010     | 11/1997 |
| WO | WO 98/00097     | 1/1998  |
| WO | WO 98/00104     | 1/1998  |
| WO | WO 98/00105     | 1/1998  |
| WO | WO 98/18438     | 5/1998  |
| WO | WO 98/42307     | 10/1998 |
| WO | WO 99/51192     | 10/1999 |

*Primary Examiner*—Shelley A. Dodson
(74) *Attorney, Agent, or Firm*—Tara L. Rachinsky

(57) ABSTRACT

A soft solid antiperspirant and/or deodorant composition comprising a volatile silicone and a behenamidoalkyl dialkylamine fatty acid as a gelling agent for the volatile silicone.

13 Claims, No Drawings

SOFT SOLID COMPOSITIONS WITH REDUCED SYNERESIS

FIELD OF THE INVENTION

This invention relates to the use of a behenamidoalkyl dialkylamine fatty acid (especially behenamidopropyl dimethylamine/behenic acid) as a gelling agent for a volatile silicone such as cyclomethicone for soft solid cosmetic products, especially antiperspirants and/or deodorants.

BACKGROUND OF THE INVENTION

Behenamidopropyl dimethylamine/behenic acid (sold under the tradename Catemol® 220-B and available from Phoenix Chemical, Inc., Somerville, N.J.) can be classified as a cationic organic salt with a small amount of free behenic acid. Trade literature for this material describes its solubility in a variety of oils at elevated temperature and its ability to dissolve heated cyclomethicone (for example, 65–70 degrees C.) and then to form an opaque gel upon cooling with a smooth emollient feel. For water/oil systems such as makeup it reduces the shiny, oily appearance on the skin.

In general, soft solids are gelled or made more solid using triglycerides, clays or silicone elastomers.

U.S. Pat. No. 5,019,375 to Tanner et al describes low residue, high viscosity antiperspirant creams comprising a volatile silicone, a particulate antiperspirant, a clay thickening agent, and a non-volatile paraffinic hydrocarbon fluid.

U.S. Pat. No. 4,526,780 to Marschner et al describes anhydrous antiperspirant paste or cream compositions comprising an oil absorbent material homogeneously dispersed in a vehicle comprising 25–55% of a volatile silicone and a clay suspending/thickening agent in the form of a gel.

U.S. Pat. No. 5,225,188 to Abrutyn et al describes underarm products comprising volatile and/or non-volatile alkylmethylsiloxanes.

U.S. Pat. No. 5,718,890 to Putnam et al describes antiperspirant cream compositions comprising selected triglyceride gellants.

U.S. Ser. No. 10/267,544 filed Oct. 9, 2002 describes a low residue antiperspirant and/or deodorant composition in the form of an anhydrous, surfactant-free and antiseptic alcohol-free suspension exhibiting a syneresis of less than 8% and comprising: a volatile silicone; a selected silicone elastomer, an antiperspirant active; and polyethylene beads having a particle size in the range of 5–40 microns and a density in the range of 0.91–0.98 g/cm$^3$.

Other references related to soft solid formulations include:

(a) particulate thickening agents such as fumed silica: for example, U.S. Pat. No. 5,069,897 to Orr; and U.S. Pat. No. 4,937,069 to Shin; and (c) selected volatile and/or non-volatile alkylmethylsiloxanes such as those including a structuring wax: for example, PCT applications WO 97/16161 and 16162 both of which are assigned to Unilever PLC.

The use of a class of compositions known as silicone elastomers in cosmetic compositions has shown some interesting results. PCT case WO 97/44010 and assigned to the same assignee as this application describes a silicone gel material made by combining (a) a volatile silicone material and (b) an organopolysiloxane material (or silicone elastomer) as a gelling agent wherein the organopolysiloxane material (silicone elastomer) can be a reaction product of a vinyl-terminated siloxane polymer and a silicon hydride cross-linking agent. Related technology is also disclosed in PCT publications WO 98/00097, WO 98/00104 and 98/00105 assigned to Unilever PLC on cross-linked non-emulsifying elastomers.

U.S. Pat. No. 5,599,533 to Stepniewski et al assigned to Estee Lauder describes a stable water-in-oil emulsion system formed with an organopolysiloxane elastomer, a vehicle in which the elastomer is dispersed or dispersible, a stabilizing agent, a surfactant and an aqueous component. A commercial product known as "REVELATION" retexturizing complex for hands and chest sold by the same assignee contains a silicone gel material with an organopolysiloxane component and octamethylcyclotetrasiloxane.

EP 0 787 758 A1 teaches a method for solvent thickening by using a silicone latex having a plurality of crosslinked polysiloxane particles.

Another recent case assigned to the same assignee as this application is PCT Publication WO 99/51192 and U.S. patent application Ser. No. 9/273,152 which describes antiperspirant compositions with the use of broad categories of elastomers. Other examples of the use of elastomer type materials and/or methods for processing such materials may be found in PCT Publications WO 98/00097; WO 98/00104; WO 98/00105; WO 98/18438; WO 98/42307 all of which are incorporated herein by reference as to elastomer materials and methods of processing such materials.

Two major problems have been observed when the use of elastomer materials is included in soft solid formulations. The first problem is reduction in efficacy due to the formation of an occlusive elastomeric film which prevents the active from diffusing into the sweat duct. The second problem is the consistency of the product as evidenced by high viscosity and elastic behavior when applied to the surface of the skin.

Thus, it is an object of the invention to provide improved cosmetic compositions with reduced syneresis. It is a further object to provide soft solid antiperspirant/deodorant products that have low residue, especially on clothing. It is yet another object to provide a soft solid that is made with gelled cyclomethicone and cationic organic salts. These and other objects of the invention will be apparent from the following description of the invention.

BRIEF SUMMARY OF THE INVENTION

The invention comprises the use of a behenamidoalkyl dialkylamine fatty acid (especially behenamidopropyl dimethylamine/behenic acid) as a unique gelling agent for soft solid compositions, especially antiperspirants/deodorants. The use of this gelling agent with a volatile silicone such as cyclomethicone results in reducing or eliminating syneresis. Behenamidoalkyl dialkylamine fatty acid can be represented by Formula I:

$$CH_3(CH_2)_{20}-C(O)-N(R^1)-(CH_2)_n-N^+(R^2)(R^3)-H^*X^{-1}$$ 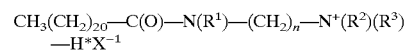

Fomula I wherein:

R$^1$=H or methyl, particularly H;

n is an average and =3–5, particularly 3;

R$^2$ and R$^3$ may be the same or different and are each independently selected from the group consisting of methyl and ethyl, particularly methyl; and $X^{-1}$=an anion which is

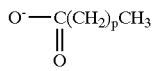

where p is a number in the range of 20–28.

A particular material of Formula I is behenamidopropyl dimethylamine/behenic acid which is sold as Catemol® 220-B wherein $R^1$=H, n=3, $R^2$ and $R^3$ are each methyl; and $X^{-1}$ is

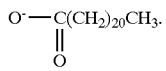

This material is a solid.

DETAILED DESCRIPTION OF THE INVENTION

The invention comprises soft solid antiperspirant/deodorant products having ≦12% syneresis and comprising:

(a) 10–88 weight % (particularly 25–75 weight % and, more particularly, 30–55 weight %) of a volatile silicone, particularly cyclomethicone, and especially D5 and/or D6 cyclomethicone;

(b) 0.5–20 weight % (particularly 8–15 weight %) of behenamidopropyl dimethylamine/behenic acid as a principal or sole gelling agent (principal meaning that the amount of behenamidopropyl dimethylamine/behenic acid used is over half of the total amount of all gelling agents used);

(c) 0.1–10 weight % of a co-gellant which is wax with a melting point in the range of 60–85 degrees C. (for example, hydrogenated castor oil, cetyl stearate, stearyl stearate, cetyl myristate, cetyl palmitate, and stearoxy dimethionine) (absent if (b) is the sole gelling agent);

(d) 1–20 weight % of an emollient;

(e) 5–25 weight % of a powdered antiperspirant active;

provided that if the amount of syneresis in greater than 12 weight % (as may happen if the amount of behenamidopropyl dimethylamine/behenic acid in the composition is less than 10 weight %), an additional ingredient which is an inert particulate material selected from the group consisting of hydrophobic silica (such as Aerosil—R974 from Degussa, Parsippany, N.J.), hydrophilic silica (such as Cabosil M-5), clays (such as kaolins, bentonites, hectorites, attapulgites and smegtites) may be added in sufficient amount so as to keep the syneresis ≦12%;

Optionally, additional ingredients will include those selected from the group consisting of one or more of fragrances, coloring agents, etc.

For the volatile silicones used in this invention, linear or cyclic materials may be used alone or in combination. Linear volatile methyl siloxanes ("VMS") have the formula $(CH_3)_3SiO\{(CH_3)_2SiO\}_ySi(CH_3)_3$. The value of y is 0–5. Cyclic VMS have the formula $\{(CH_3)_2SiO\}_z$. The value of z is 3–6. Preferably, these volatile methyl siloxanes have boiling points less than about 275 degrees C. and viscosities of about 0.65–7.0 centistokes ($mm^2/s$).

Representative linear volatile methyl siloxanes (I) are hexamethyldisiloxane (MM) with a boiling point of 100 degrees C., viscosity of 0.65 $mm^2/s$, and formula $Me_3SiOSiMe_3$; octamethyltrisiloxane (MDM) with a boiling point of 152 degrees C., viscosity of 1.04 $mm^2/s$, and formula $Me_3SiOMe_2SiOSiMe_3$; decamethyltetrasiloxane ($MD_2M$) with a boiling point of 194 degrees C., viscosity of 1.53 $mm^2/s$, and formula $Me_3SiO(Me_2SiO)_2SiMe_3$; dodecamethylpentasiloxane ($MD_3M$) with a boiling point of 229 degrees C., viscosity of 2.06 $mm^2/s$, and formula $Me_3SiO(Me_2SiO)_3SiMe_3$; tetradecamethylhexasiloxane ($MD_4M$) with a boiling point of 245 degrees C., viscosity of 2.63 $mm^2/s$, and formula $Me_3SiO(Me_2SiO)_4SiMe_3$; and hexadecamethylheptasiloxane ($MD_5M$) with a boiling point of 270 degrees C., viscosity of 3.24 $mm^2/s$, and formula $Me_3SiO(Me_2SiO)_5SiMe_3$.

Representative cyclic volatile methyl siloxanes (II) are hexamethylcyclotrisiloxane ($D_3$) a liquid with a boiling point of 134 degrees C. and formula $\{(Me_2)SiO\}_3$; octamethylcyclotetrasiloxane ($D_4$) with a boiling point of 176 degrees C., viscosity of 2.3 $mm^2/s$, and formula $\{(Me_2)SiO\}_4$; decamethylcyclopentasiloxane ($D_5$) with a boiling point of 210 degrees C., viscosity of 3.87 $mm^2/s$, and formula $\{(Me_2)SiO\}_5$; and dodecamethylcyclohexasiloxane ($D_6$) with a boiling point of 245 degrees C., viscosity of 6.62 $mm^2/s$, and formula $\{(Me_2)SiO\}_6$ (with a particular group of cyclics including D5 and D6 cyclomethicones).

Particular examples of suitable volatile silicones include DC-244 Fluid, DC-245 Fluid, DC 246 Fluid, DC-344 Fluid, DC-345 Fluid, DC 200 Fluid (with 0.65 cst viscosity) to DC 200 Fluid (with 5 cst viscosity), and DC-1184 Fluid (a mixture of low molecular weight volatile and non-volatile silicones most of which are linear and volatile, such material has a boiling point greater than 35 degrees and a viscosity of about 1.6 centistokes) all of which are from Dow Corning Corp.), and especially decamethylcyclopentasiloxane (DC-245 Fluid).

Emollients are a known class of materials in this art, imparting a soothing effect to the skin. These are ingredients which help to maintain the soft, smooth, and pliable appearance of the skin. Emollients are also known to reduce whitening on the skin and/or improve aesthetics. Examples of chemical classes from which suitable emollients can be found include:

(a) fats and oils which are the glyceryl esters of fatty acids, or triglycerides, normally found in animal and plant tissues, including those which have been hydrogenated to reduce or eliminate unsaturation. Also included are synthetically prepared esters of glycerin and fatty acids. Isolated and purified fatty acids can be esterified with glycerin to yield mono-, di-, and triglycerides. These are relatively pure fats which differ only slightly from the fats and oils found in nature. The general structure may be represented by Formula III:

Formula III

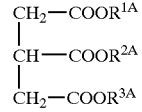

wherein each of $R^{1A}$, $R^{2A}$, and $R^{3A}$ may be the same or different and have a carbon chain length (saturated or unsaturated) of 7 to 30. Specific examples include peanut oil, sesame oil, avocado oil, coconut, cocoa butter, almond oil, safflower oil, corn oil, cotton seed oil, castor oil, hydrogenated castor oil, olive oil, jojoba oil, cod liver oil, palm oil, soybean oil, wheat germ oil, linseed oil, and sunflower seed oil;

(b) hydrocarbons which are a group of compounds containing only carbon and hydrogen. These are derived from petrochemicals. Their structures can vary widely and include aliphatic, alicyclic and aromatic compounds. Specific examples include paraffin, petrolatum, hydrogenated polyisobutene, and mineral oil.

(c) esters which chemically, are the covalent compounds formed between acids and alcohols. Esters can be formed from almost all acids (carboxylic and inorganic) and any alcohol. Esters here are derived from carboxylic acids and an alcohol. The general structure would be $R^{4A}CO-OR^{5A}$. The chain length for each of $R^{4A}$ and $R^{5A}$ can vary from 7 to 30 and can be saturated or unsaturated, straight chained, branched or a phenyl or benzyl group. Specific examples include isopropyl myristate, isopropyl palmitate, isopropyl stearate, isopropyl isostearate, butyl stearate, octyl stearate, hexyl laurate, cetyl stearate, diisopropyl adipate, isodecyl oleate, diisopropyl sebacate, isostearyl lactate, $C_{12-15}$ alkyl benzoates, myreth-3 myristate, dioctyl malate, neopentyl glycol diheptanoate, neopentyl glycol dioctanoate, dipropylene glycol dibenzoate, $C_{12-15}$ alcohols lactate, isohexyl decanoate, isohexyl caprate, diethylene glycol dioctanoate, octyl isononanoate, isodecyl octanoate, diethylene glycol diisononanoate, isononyl isononanoate, isostearyl isostearate, behenyl behenate, $C_{12-15}$ alkyl fumarate, laureth-2 benzoate, propylene glycol isoceteth-3 acetate, propylene glycol ceteth-3 acetate, octyldodecyl myristate, cetyl ricinoleate, myristyl myristate.

(d) saturated and unsaturated fatty acids which are the carboxylic acids obtained by hydrolysis of animal or vegetable fats and oils. These have general structure $R^{6A}COOH$ with the $R^{6A}$ being a hydrocarbon group having a carbon chain length from 7–20 carbons and are straight chain or branched.

(e) saturated and unsaturated fatty alcohols (including guerbet alcohols) with general structure $R^{7A}COH$ where $R^{7A}$ can be straight chain or branched and have carbon length of 7 to 20.

(f) lanolin and its derivatives which are a complex esterified mixture of high molecular weight esters of (hydroxylated) fatty acids with aliphatic and alicyclic alcohols and sterols. General structures would include $R^{8A}CH_2-(OCH_2CH_2)_n OH$ where $R^{8A}$ represents the fatty groups derived from lanolin and n=5 to 75 or $R^{9A}CO-(OCH_2CH_2)_n OH$ where $R^{9A}CO$— represents the fatty acids derived from lanolin and n=5 to 100. Specific examples include lanolin, lanolin oil, lanolin wax, lanolin alcohols, lanolin fatty acids, isopropyl lanolate, ethoxylated lanolin and acetylated lanolin alcohols.

(g) alkoxylated alcohols wherein the alcohol portion is selected from aliphatic alcohols having 2–18 and more particularly 4–18 carbons, and the alkylene portion is selected from the group consisting of ethylene oxide, and propylene oxide having a number of alkylene oxide units from 2–53 and, more particularly, from 2–15. Specific examples include PPG-14 butyl ether and PPG-53 butyl ether.

(h) silicones and silanes which are the linear organo-substituted polysiloxanes which are polymers of silicon/oxygen with general structure:

(1) $(R^{10})_3 SiO(Si(R^{11})_2 O)_x Si(R^{12})_3$ where $R^{10}$, $R^{11}$ and $R^{12}$ can be the same or different and are each independently selected from the group consisting of C1–C10 alkyl;

(2) $HO(R^{14})_2 SiO(Si(R^{15})_2 O)_x Si(R^{16})_2 OH$, where $R^{14}$, $R^{15}$ and $R^{16}$ can be the same or different and are each independently selected from the group consisting C1–C10 alkyl; or (3) organo-substituted silicone compounds of formula $(R^{17})(R^{18})(R^{19})Si-O-Si(R^{20})(R^{21})(R^{22})$ which are not polymeric where each of $R^{17}$, $R^{18}$ $R^{19}$, $R^{20}$, $R^{21}$, and $R^{22}$ can be the same or different and are each independently selected from the group consisting of phenyl and C1–C60 alkyl optionally with one or both of the terminal R groups also containing an hydroxyl group. Specific examples include dimethicone, dimethiconol behenate, $C_{30-45}$ alkyl methicone, stearoxytrimethylsilane, phenyl trimethicone and stearyl dimethicone.

(i) mixtures and blends of two or more of the foregoing.

One particular group of emollients includes C12–15 alkyl benzoate (FINSOLV TN from Finetex Inc., Elmwood Park, N.J.), medium volatility dimethicone (especially 10–350 centistoke material and more especially 10–50 centistoke material), PEG-8 distearate, isopropyl myristate, PPG-3-myristyl ether, and polyisobutene 250, and neopentyl glycol diheptanoate.

The emollient or emollient mixture or blend thereof incorporated in compositions according to the present invention can, illustratively, be included in amounts of 1–20%, and particularly 5–17% by weight of the total weight of the composition.

The antiperspirant active used in this invention will be in powder form. These actives include conventional aluminum and aluminum/zirconium salts, as well as aluminum/zirconium salts complexed with a neutral amino acid such as glycine, as known in the art. See each of European Patent 0 512 770 B1 and PCT case WO 92/19221, the contents of each of which are incorporated herein by reference in their entirety, for disclosure of antiperspirant active materials. Suitable materials include (but are not limited to) aluminum chlorides (various types including, for example, anhydrous form, hydrated form, etc.), zirconyl hydroxychlorides, zirconyl oxychlorides, basic aluminum chlorides, basic aluminum chlorides combined with zirconyl oxychlorides and hydroxychlorides, and organic complexes of each of basic aluminum chlorides with or without zirconyl oxychlorides and hydroxychlorides and mixtures of any of the foregoing. These include, by way of example (and not of a limiting nature), aluminum chlorohydrate, aluminum chloride, aluminum sesquichlorohydrate, aluminum chlorohydrol-propylene glycol complex, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum dichlorohydrate, aluminum chlorohydrex PG, aluminum chlorohydrex PEG, aluminum dichlorohydrex PG, aluminum dichlorohydrex PEG, aluminum zirconium trichlorohydrex gly propylene glycol complex, aluminum zirconium trichlorohydrex gly dipropylene glycol complex, aluminum zirconium tetrachlorohydrex gly propylene glycol complex, aluminum zirconium tetrachlorohydrex gly dipropylene glycol complex, and mixtures of any of the foregoing. The aluminum-containing materials can be commonly referred to as antiperspirant active aluminum salts. Generally, the foregoing metal antiperspirant active materials are antiperspirant active metal salts. In the embodiments which are antiperspirant compositions according to the present invention, such compositions need not include aluminum-containing metal salts, and can include other antiperspirant active materials, including other antiperspirant active metal salts. Generally, Category I active antiperspirant ingredients listed in the Food and Drug Administration's Monograph on antiperspirant drugs for over-the-counter human use can be used. In addition, any new drug, not listed in the Monograph, such as tin or titanium salts used alone or in combination with aluminum compounds (for example, aluminum-stannous chlorohydrates), aluminum nitratohydrate and its combination with zirconyl hydroxychlorides and nitrates, can be incorporated as an antiperspirant active ingredient in antiperspirant compositions according to the present invention. Preferred antiperspirant actives that can be incorporated in the compositions of the present invention include the enhanced efficacy aluminum salts and the enhanced efficacy aluminum/zirconium salt-glycine materials, having enhanced efficacy due to improved molecular distribution, known in the art and discussed, for example, in PCT No. WO92/19221, the contents of which are incorporated by reference in their entirety herein. Particular actives include Westchlor ZR 35B aluminum zirconium tetrachlorohydrex gly (from Westwood Chemical Corporation, Middletown, N.Y.), and Rezal 36 GP and AZP 902 aluminum zirconium tetrachlorhydrex gly (both from Reheis, Berkeley Heights, N.J.) as well as Rezal AZP 908 from Reheis and aluminum zirconium tetrachlorhydrex gly (Z576 from Summit Research Labs, Huguenot, N.Y.). In general, the metal: chloride mole ratio is in the range of 2.1–0.9:1 for such salts.

In one particular type of salt of interest, an aluminum zirconium tetra salt with glycine is used wherein aluminum zirconium tetrachlorohydrex glycine salt having a metal to chloride ratio in the range of 0.9–1.2:1 (especially in the range of 0.9–1.1:1 and, more particularly in the range of 0.9–1.0:1); and a glycine:zirconium mole ratio greater than 1.3:1, particularly greater than 1.4:1. This type of salt may be made in a variety of ways as described in U.S. Pat. No. 6,375,937 owned by the same owner as this application.

Syneresis is evaluated using the method described in the Examples.

Soft solid antiperspirant products may be created in accordance with this invention.

Gels, pastes and creams (which are also known as soft-solids or semi-solids) can be suitably packaged in containers which have the appearance of a stick, but which dispense through apertures (for example, slots or pores) on the top surface of the package. These products have been called soft sticks or "smooth-ons". Reference is made to U.S. Pat. No. 5,102,656 to Kasat, U.S. Pat. No. 5,069,897 to Orr, and U.S. Pat. No. 4,937,069 to Shin.

A representative composition which can be dispensed through apertures is described in U.S. Pat. No. 5,102,656 to Kasat. This disclosed composition is a creamy, heterogeneous anhydrous antiperspirant product containing, in percent by weight, of the total weight of the composition, 30% –70% of a volatile silicone as a carrier, 7–30% of a suitable gelling agent or agents, and about 12–30% of a physiologically acceptable antiperspirant agent. This patent discloses that the gelling agent can be any of a number of materials, including, for example, hydrogenated vegetable oil, hydrogenated castor oil, fatty acids having from 14 to 36 carbon atoms, beeswax, paraffin wax, fatty alcohols having from 14 to 24 carbon atoms, polyethylene and the like.

Compositions according to the present invention can be made by mixing the silicone with the gelling agent or viscosity modifier, the antiperspirant active ingredient and optionally one or more of emollient(s), thickener(s) and fragrance. Mixing conditions and the amount of heating will depend on what types of materials are being combined. For soft solid/cream products made with waxes with a melting point in the range of 60–85 degrees C. temperatures from 60 to 85 degrees C. should be used. The mixture can be introduced into dispensing containers known to those skilled in the art. In one particular example, slotted dispensers may be used such as those known in the art, for example, those having a parallel row or rows of straight or curved slots or holes with a screw mechanism for forcing the composition through the top as the product is used.

The types of packaging used for dispensing such products (usually by rubbing the product under the arm in the axillary region) are well known. Where the dispensing containers have a top surface with slots therein, the composition can be rubbed onto the skin from the top surface of the container (itself fed from a reservoir of product in the container) so as to deposit an adequate amount of the cosmetic composition on to the skin. The cosmetic composition, for example, an antiperspirant and/or deodorant in the form of a soft solid, can be extruded from inside the dispensing container through the slots or holes onto the top of the surface of the dispensing container, and from there may be applied to the skin in the axillary regions to deposit sufficient amounts of antiperspirant and/or deodorant active material to reduce body malodor and/or reduce perspiration in axillary regions of the human body.

In accordance with the present invention, examples of sample formulations include:

Formulation A
6–12 weight % Catemol 220B
3–8 weight % co-gellant with a melting point greater than 60 degrees C. and less than 85 degrees C. such as hydrogenated castor oil MP 80
1–4 weight % of a particulate such as Cabosil M-5
40–65 weight % of a volatile silicone such as D5 and/or D6 cyclomethicone
10–20 weight % of an emollient such as C12–15 alkyl benzoate, PEG-8 distearate, or mixtures thereof
15–25 weight % of an antiperspirant active
optionally 0.5–1.5 weight % fragrance Formulation B
8–15 weight % Catemol 220B
2–5 weight % co-gellant with a melting point greater than 60 degrees C. and less than 85 degrees C. such as hydrogenated castor oil MP 80
35–55 weight % of a volatile silicone such as D5 and/or D6 cyclomethicone
12–18 weight % of an emollient such as C12–15 alkyl benzoate, PEG-8 distearate, or mixtures thereof
15–25 weight % of an antiperspirant active
optionally 0.5–1.5 weight % fragrance Throughout the present specification, where compositions are described as including or comprising specific components or materials, or where methods are described as including or comprising specific steps, it is contemplated by the inventors that the compositions of the present invention also consist essentially of, or consist of, the recited components or materials, and also consist essentially of, or consist of, the recited steps. Accordingly, throughout the present disclosure any described composition of the present invention can consist essentially of, or consist of, the recited components or materials, and any described method of the present invention can consist essentially of, or consist of, the recited steps.

EXAMPLES

The following Examples are offered as illustrative of the invention and are not to be construed as limitations thereon. In the Examples and elsewhere in the description of the invention, chemical symbols and terminology have their usual and customary meanings. In the Examples as elsewhere in this application values for n, m, etc. in formulas, molecular weights and degree of ethoxylation or propoxylation are averages. Temperatures are in degrees C. unless otherwise indicated. The amounts of the components are in weight percents based on the standard described; if no other standard is described then the total weight of the composition is to be inferred. Various names of chemical components include those listed in the *CTFA International Cosmetic Ingredient Dictionary* (Cosmetics, Toiletry and Fragrance Association, Inc., 7$^{th}$ ed. 1997).

Examples 1–6: Soft Solid

Formulation—Using the types and amounts of ingredients listed in TABLE A, 300 gram samples are made. Cyclomethicone (D5 cyclomethicone as DC 345 from Dow Corning Corp., Midland, Mich.) and C12–15 alkyl benzoate (FINSOLV TN from Finetex Inc., Elmwood Park, N.J.) are placed in a 500 ml beaker. This mixture (which also may be viewed as solvents) is heated to a temperature in the range of 65–70 degrees C. and the behenamidopropyl dimethyl amine behenate (CATEMOL® 220-B from Phoenix Chemical, Inc., Somerville, N.J.) is added with stirring using a Lightnin' Mixer (Model DS1010 from Harington-Robb, Moorestown, N.J.) until the material is dissolved. PEG-8 distearate is then added and stirring is continued until it is dissolved. The beaker as the reaction vessel is then heated to a temperature in the range of 75–80 degrees C. and the castor oil is added and stirred until dissolved. The reaction vessel is cooled to 75 degrees C. and the antiperspirant active (AZP 908 from Reheis) and the hydrophilic silica (CABOSIL M-5 from Cabot Corp., Tuscola, Ill.) (if used) are each added sequentially. The mixture is stirred for 15 minutes and then cooled to 70–72 degrees C. The fragrance is then added and the mixture is poured at 70–72 degrees C. into appropriate containers such as those known in the art for use with soft solids (ovoid packages, for example, 10 cm height×6 cm width at longer axis×4 cm width at shorter axis for oval, with multiple openings as holes or parallel slots in the top of the package sufficient in size to allow for product to be extruded through the opening (for example 2–5 mm) as pressure is applied, such as by a turning means at the bottom of the package). In TABLE A all amounts are in % by weight based on the entire weight of the composition.

Syneresis—Samples (10 grams) of soft solids made in Examples 1–4 are placed into 25 gram vials. The samples are placed in an oven at 50 degrees C. for 3 days. The samples are then removed from the oven, cooled for 1 hour, and centrifuged for 20 minutes at 4000 rpm (Beckman-Coulter ALLEGRA™ 6 centrifuge). Any residual solvent is then removed with a disposable plastic pipette and weighed. Percent syneresis is calculated using the following formula:

(weight of solvent removed with pipette)×100/initial weight of sample

The results are in TABLE A.

Reflectance Measurement (L*)—In order to evaluate whiteness residue, the L* value was determined using a Hunter Lab Reflectometer (Hunter Associates Inc., Reston, Va.). This equipment utilizes a three-axis opponent scale system, based on the theory that color is perceived by black-white (L), red-green (a) and yellow-blue (b) sensations. If, for example, a fabric undergoes a washing treatment, then a +ΔL indicates that the sample is lighter or whiter in color, a +Δa indicates a redder or less green sample, and +Δb value indicates a yellower or less blue sample. If the signs are negative, the corresponding color changes are darker, greener and bluer, respectively. For prediction of whiteness residue on skin of antiperspirant products, only the L* value is used. In the methodology developed here, a sample (0.20 gram) of an antiperspirant product is applied to a 5.5 cm diameter black cover (from a 113.5 gram, 4 ounce jar). The product is spread evenly with a finger cot and the cover is reweighed to a final weight of 0.17 gram. L*, a,b values are measured using the Hunter Lab Reflectometer and the L* value is used to determine whiteness level. The higher the number the whiter the surface and the greater the residue. The L* values are in TABLE A.

TABLE A

| Ingredient | Ex. 1 | Ex. 2 | Ex. 3 | Ex. 4 | Ex. 5 | Ex. 6 |
|---|---|---|---|---|---|---|
| Cyclomethicone (DC 345) | 46.80 | 37.80 | 32.80 | 44.30 | 41.80 | 50.30 |
| C12–15 alkyl benzoate (FINSOLV TN) | 12.00 | 12.00 | 12.00 | 12.00 | 12.00 | 6.00 |
| Hydrogenated castor oil MP 80 | 4.00 | 8.00 | 8.00 | 4.00 | 4.00 | 4.00 |
| PEG-8 distearate | 4.00 | 4.00 | 4.00 | 4.00 | 4.00 | 4.00 |
| AP active (AZP 908) | 22.00 | 22.00 | 22.00 | 22.00 | 22.00 | 22.00 |
| Fragrance | 1.20 | 1.20 | 1.20 | 1.20 | 1.20 | 1.20 |
| Behenamidopropyl dimethyl amine behenate (CATEMOL ® 220-B) | 10.00 | 15.00 | 20.00 | 10.00 | 10.00 | 10.00 |
| Hydrophilic silica (CABOSIL M-5) | 0 | 0 | 0 | 2.50 | 5.00 | 2.50 |
| Total | 100 | 100 | 100 | 100 | 100 | 100 |
| % Syneresis | 9.1 | 0 | 0 | 2.5 | 0.0 | 2.3 |
| Reflectance Value (L*) | 35.29 | 34.71 | 31.05 | 35.44 | 34.16 | 34.51 |

Examples 7–12

The method described for Examples may be repeated with the same amount of active, but substituting aluminum zirconium tetrachlorhydrex glycine (Z756 from Summit) for the AZP 908.

We claim:

1. A soft solid antiperspirant and/or deodorant composition comprising a volatile silicone and a behenamidoalkyl dialkylamine fatty acid of Formula I as a gelling agent:

$$CH_3(CH_2)_{20}-C(O)-N(R^1)-(CH_2)_n-N^+(R^2)(R^3)-H*X^{-1} \quad \text{Formula I}$$

wherein:
$R^1$=H or methyl;
n is an average and=3–5;
$R^2$ and $R^3$ may be the same or different and are each independently selected from the group consisting of methyl and ethyl; and
$X^{-1}$=

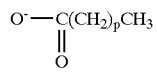

where p is a number in the range of 20–28.

2. A composition according to claim 1 wherein $R^1$=H.

3. A composition according to claim 1 wherein n is an average and=3.

4. A composition according to claim 1 wherein $R^2$ and $R^3$ are each methyl.

5. A composition according to claim 1 wherein $R^1$=H, n is an average and=3, and $R^2$ and $R^3$ are each methyl.

6. A composition according to claim 1 having ≦12% syneresis and comprising:
   (a) 10–88 weight % of a volatile silicone;
   (b) 0.5–20 weight % of behenamidoalkyl dialkylamine fatty acid of Formula I as a principal gelling agent;
   (c) 0.1–10 weight % of a co-gellant which is wax with a melting point in the range of 60–85 degrees C. (for example, hydrogenated castor oil, cetyl stearate, stearyl stearate, cetyl myristate, cetyl palmitate, and stearoxy dimethionine);
   (d) 1–20 weight % of an emollient;
   (e) 5–25 weight % of a powdered antiperspirant active; provided that if the amount of syneresis in greater than 12 weight %, an additional ingredient which is an inert particulate material selected from the group consisting of hydrophobic silica, hydrophilic silica, and clays may be added in sufficient amount so as to keep the syneresis ≦12%.

7. A composition according to claim 6 comprising:
   (a) 25–75 weight % of the volatile silicone; and
   (b) 8–15 weight % the behenamidoalkyl dialkylamine fatty acid.

8. A composition according to any one of claims 1–7 wherein the volatile silicone is cyclomethicone.

9. A composition according to claim 6 or 7 wherein $R^1$=H, n is an average and=3, and $R^2$ and $R^3$ are each methyl.

10. A composition according to claim 1 or 6 wherein the emollient is selected from the group consisting of:
   (a) fats and oils of Formula III:

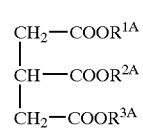

wherein each of $R^{1A}$, $R^{2A}$, and $R^{3A}$ may be the same or different, are saturated or unsaturated and have a carbon chain length of 7 to 30;
   (b) hydrocarbons selected from the group consisting of paraffin, petrolatum, hydrogenated polyisobutene, and mineral oil;
   (c) esters selected from the group consisting of $R^{4A}CO-OR^{5A}$ wherein each of $R^{4A}$ and $R^{5A}$ can vary from 7 to 30 carbons and can be saturated or unsaturated, straight chained, branched or a phenyl or benzyl group;
   (d) saturated and unsaturated fatty acids of formula $R^{6A}COOH$ wherein $R^{6A}$ is a straight chain or branched hydrocarbon having 7–20 carbons;
   (e) saturated and unsaturated fatty alcohols of formula $R^{7A}COH$ where $R^{7A}$ is a straight chain or branched hydrocarbon having 7–20 carbons;
   (f) lanolin and lanolin derivatives selected from the group consisting of lanolin, lanolin oil, lanolin wax, lanolin alcohols, lanolin fatty acids, isopropyl lanolate, ethoxylated lanolin and acetylated lanolin alcohols;
   (g) alkoxylated alcohols wherein the alcohol portion is selected from aliphatic alcohols having 2–18 carbons, and the alkylene portion is selected from the group consisting of ethylene oxide, and propylene oxide having a number of alkylene oxide units from 2–53;
   (h) silicones and silanes which are the linear organo-substituted polysiloxanes which are polymers of silicon/oxygen with a general structure selected from the group consisting of:
      (1) $(R^{10})_3SiO(Si(R^{11})_2O)_xSi(R^{12})_3$ where $R^{10}$, $R^{11}$ and $R^{12}$ can be the same or different and are each independently selected from the group consisting of C1–C10 alkyl;
      (2) $HO(R^{14})_2SiO(Si(R^{15})_2O)_xSi(R^{16})_2OH$, where $R^{14}$, $R^{15}$ and $R^{16}$ can be the same or different and are each independently selected from the group consisting C1–C10 alkyl; or
      (3) organo-substituted silicone compounds of formula $(R^{17})(R^{18})(R^{19})$ Si—O—Si$(R^{20})(R^{21})(R^{22})$ which are not polymeric where each of $R^{17}$, $R^{18}R^{19}$, $R^{20}$, $R^{21}$, $R^{22}$ can be the same or different and are each independently selected from the group consisting of phenyl and C1–C60 alkyl optionally with one or both of the terminal R groups also containing an hydroxyl group; and
   (i) mixtures and blends of two or more of the foregoing.

11. A composition according to claim 1 or claim 6 wherein the emollient is selected from the group consisting of C12–15 alkyl benzoate, medium volatility dimethicone, PEG-8 distearate, isopropyl myristate, PPG-3-myristyl ether, polyisobutene 250, and neopentyl glycol diheptanoate.

12. A composition according to claim 1 comprising:
   6–12 weight % of the behenamidoalkyl dialkylamine fatty acid of claim 5;

3–8 weight % of a co-gellant which is hydrogenated castor oil MP 80;
1–4 weight % of a hydrophobic silica;
40–65 weight % of a D5 and/or D6 cyclomethicone as the volatile silicone;
10–20 weight % of an emollient selected from the group consisting of C12–15 alkyl benzoate, PEG-8 distearate, or mixtures thereof;
15–25 weight % of the antiperspirant active; and
optionally 0.5–1.5 weight % fragrance.

13. A composition according to claim 1 comprising:
8–15 weight % of the behenamidoalkyl dialkylamine fatty acid of claim 5;
2–5 weight % co-gellant which is hydrogenated castor oil MP 80;
35–55 weight % of a D5 and/or D6 cyclomethicone as the volatile silicone;
12–18 weight % of an emollient selected from the group consisting of C12–15 alkyl benzoate, PEG-8 distearate, or mixtures thereof;
15–25 weight % of the antiperspirant active; and
optionally 0.5–1.5 weight % fragrance.

* * * * *